(12) United States Patent
Huang et al.

(10) Patent No.: US 7,510,642 B2
(45) Date of Patent: Mar. 31, 2009

(54) BIOSENSOR WITH IMPROVED READING RESOLUTION

(76) Inventors: Yin-Chun Huang, 6F, No. 72-11, Lane 531, Sec. 1, Kuang-Fu Rd., Hsin-Chu City (TW); Kuo-Jeng Wang, 14, Kung-An St., Hsiao-Kang, Kaohsiung City (TW)

( * ) Notice: Subject to any disclaimer, the term of this patent is extended or adjusted under 35 U.S.C. 154(b) by 616 days.

(21) Appl. No.: 10/739,415

(22) Filed: Dec. 19, 2003

(65) Prior Publication Data

US 2004/0132203 A1 Jul. 8, 2004

(30) Foreign Application Priority Data

Dec. 31, 2002 (TW) .............................. 91138112 A

(51) Int. Cl.
*G01N 27/327* (2006.01)
(52) U.S. Cl. ..................... 205/777.5; 205/792
(58) Field of Classification Search ........................ 204/403.01–403.15; 205/777.5, 778, 792; 702/19, 702/22, 23
See application file for complete search history.

(56) References Cited

U.S. PATENT DOCUMENTS

| | | | | |
|---|---|---|---|---|
| 4,246,343 A | * | 1/1981 | Wilkins et al. ........... | 205/777.5 |
| 4,891,104 A | * | 1/1990 | Liston et al. ........... | 204/403.05 |
| 5,108,576 A | * | 4/1992 | Malmros et al. ......... | 205/777.5 |
| 7,160,251 B2 | * | 1/2007 | Neel et al. .................. | 600/365 |

OTHER PUBLICATIONS

Wentzell et al. ("Signal Processing in Analytical Chemistry," in Encyclopedia of Analytical Chemistry, pp. 9764-9800 (1-36).*

* cited by examiner

*Primary Examiner*—Alex Noguerola
(74) *Attorney, Agent, or Firm*—Stolowitz Ford Cowger LLP

(57) ABSTRACT

A method for improving a reading resolution of a biosensor is provided. The present invention includes applying a specimen on a chip of a biosensor, and a voltage-time discharge curve is established in response to a specific component in the specimen detected by the chip. Using a voltage $V_0$ of a sampling time $t_0$ of the voltage-time discharge curve as a central voltage, and selecting a plurality of respective voltages of sampling times close to the sampling time $t_0$. Obtaining an average voltage of the central voltage $V_0$ and these selected respective voltages to serve as an output voltage of the sampling time $t_0$. Determining a respective average voltage corresponding to each sampling time of the voltage-time discharge curve before the time of discharge ending based on the former step, to serve as the output voltage of the each sampling time. The each output voltage is converted to a set of digital signals. A reading of the concentration of the specific component in the specimen is determined in accordance with these digital signals.

20 Claims, 4 Drawing Sheets

BIOSENSOR WITH IMPROVED READING RESOLUTION

BACKGROUND OF THE INVENTION

1. Field of the Invention

The present invention relates to a method for sampling a measuring value of a biosensor, and more particularly to a method for improving a reading resolution of a biosensor.

2. Description of the Prior Art

In recent years, various kinds of biosensors utilizing a specific catalytic action of enzymes have been developed to be used for clinical purposes. Most valuable use of such biosensors may be made in the area of e.g. diabetes treatment where it is vital for patients to keep their blood glucose concentration ("blood sugar level" below) within a normal range. For an inpatient, the blood sugar level can be kept normal under the supervision of the doctor. For an outpatient, self-control of the blood sugar level is an important factor for treatment in lack of doctor's direct supervision.

The self-control of the blood sugar level is achieved through a diet, exercise and medication. These treatments may often be simultaneously employed under the supervision of the doctor. It has been found that the self-control works more effectively when the patient himself is able to check whether or not his blood sugar level is within the normal range.

Recently, blood sugar determining instruments have been used for self-checking of blood sugar level. As shown in FIG. 1, a blood sugar determining instrument mainly includes a main detecting unit 10 and a chip 12 for blood sugar measurement. As shown in FIG. 2, the chip 12 includes a strip-like substrate 122 provided in its front portion with an electrode section 1221. The electrode section 1221 is covered by a reaction layer 124, a spacer 126 and a cover sheet 128. The electrode section 1221 is provided with an operational terminal 1222 and a counterpart terminal 1224 surrounding the operational terminal 1222. The operational terminal 1222 and the counterpart terminal 1224 are electrically connected to lead terminals 1226 and 1228, respectively, which are formed on a base end portion of the strip-like substrate 122. The reaction layer 124, which covers the electrode section 1221, contains potassium ferricyanide and an oxidase such as glucose oxidase.

The blood sugar determining instruments may be used in the following manner. A patient pricks his or her own skin with e.g. a lancet for oozing blood. Then, the oozed-out blood is caused to touch the tip of the chip 12 plugged into the main detecting unit 1. The blood is partially sucked into the reaction layer 124 by capillary action. The reaction layer 124 disposed above the electrode section 1221, is dissolved by the blood, which starts an enzyme reaction, as the following formula:

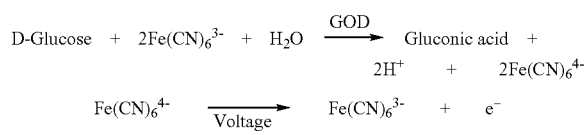

Potassium ferrocyanide is produced in an amount corresponding to the glucose concentration. After a certain period of time, a predetermined voltage $V_{ref}$ is applied on the chip 12 to electrochemically oxidize potassium ferrocyanide to release electrons. A response current is generated and passes through the operational terminal 1222. The response current is proportional to the concentration of potassium ferrocyanide produced by the enzyme reaction or to the concentration of the glucose. Therefore, the blood sugar level can be known by measuring the response current.

FIG. 3 is a schematic diagram of a control circuit of the blood sugar determining instrument of FIG. 1, in which the electrode section 1221 of the chip 12 can be regarded as a resistor $R_s$. The voltage $V_{ref}$ to be applied can be provided by a battery. The response current I generated by the chip 12 decays as time progresses to form a time-dependent discharge curve corresponding to the glucose concentration of the blood. Moreover, the response current I of each sampling time of the time-dependent discharge curve is converted to an output voltage $V_{out}$ by a current/voltage converter 32 having an amplification resistance Rf. As a consequence, the response currents I decaying as time progresses form a voltage-time discharge curve. Each voltage of each sampling time of the voltage-time discharge curve is converted to a set of digital signals by an analog to digital converter 34. A microprocessor 36 reads the digital signals output from the analog to digital converter 34, and calculates the glucose concentration of the blood in accordance with the digital signals. A reading of the glucose concentration is displayed on a display such as a liquid crystal display (LCD) 38.

The output voltage $V_{out}$ for each sampling time of the voltage-time discharge curve is an integer value, whose value is in the range of 0~255 mv. As a consequence, the resolution of readings of the conventional blood sugar determining instrument is limited. That is, the output voltage for each sampling time of the voltage-time discharge curve can not have accuracy to decimal point. The resolution of readings of the conventional blood sugar determining instrument hence can not be improved.

SUMMARY OF THE INVENTION

It is one objective of the present invention to provide a method for improving a reading resolution of a biosensor, which utilizes a multi-sampling method to obtain an average value having accuracy to decimal point as an output of a measuring value. Accordingly, the reading resolution of the biosensor can be improved.

It is another objective of the present invention to provide a method for improving a reading resolution of a biosensor, which does not need additional elements incorporated in, the purpose of cost down can be attained.

It is a further objective of the present invention to provide a method for improving a reading resolution of a biosensor, which utilizes a multi-sampling method to obtain an average for each measuring value to reduce noise interference.

In order to achieve the above objectives of this invention, the present invention provides a method for improving a reading resolution of a biosensor. A specimen is applied on a chip of a biosensor. The chip generates a time-varying response current in response to a specific component of the specimen, so that a voltage-time discharge curve is established in response to the specific component of the specimen. Using a voltage $V_0$ of a sampling time $t_0$ of the voltage-time discharge curve as a central voltage, and selecting a plurality of respective voltages whose sampling times close to the sampling time $t_0$. Obtaining an average voltage of the central voltage $V_0$ and the respective voltages to serve as an output voltage corresponding to the sampling time $t_0$. Obtaining an average voltage corresponding to each sampling time of the voltage-time discharge curve before the time of discharge ending to serve as an output voltage of the each sampling time based on the former step. Converting the output voltage of the each sampling time of the voltage-time discharge curve to a set of binary digital signals. Determining a reading of a concentration of the specific component in accordance with the sets of binary digital signals before the time of discharge ending.

The present invention selects several neighboring voltages of a voltage-time discharge curve of a specific component of a specimen, and obtains an average voltage of these neighboring voltages to serve as an output voltage of a selected sampling time among the sampling times corresponding to these neighboring voltages. As a result, the output of each measuring value of the biosensor can have accuracy to decimal point. The reading resolution of the biosensor can thus be improved and the noise interference of the output of each measuring value also can be reduced.

BRIEF DESCRIPTION OF THE DRAWINGS

The objectives and features of the present invention as well as advantages thereof will become apparent from the following detailed description, considered in conjunction with the accompanying drawings.

DESCRIPTION OF THE PREFERRED EMBODIMENTS

Figure 1:
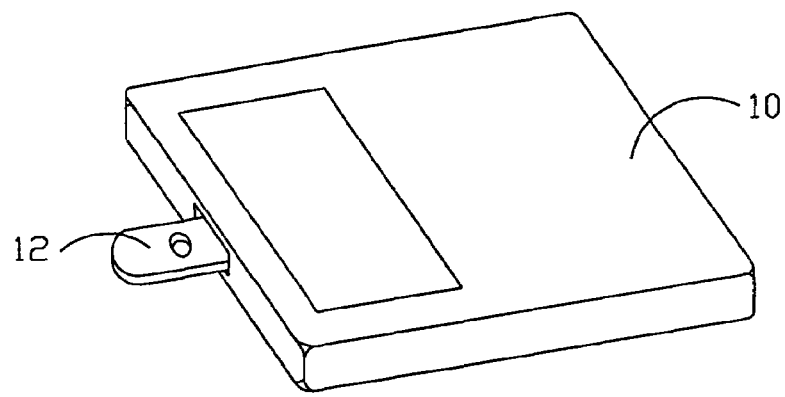
FIG. 1 is a schematic perspective view of a conventional blood sugar determining instrument.
Figure 2:
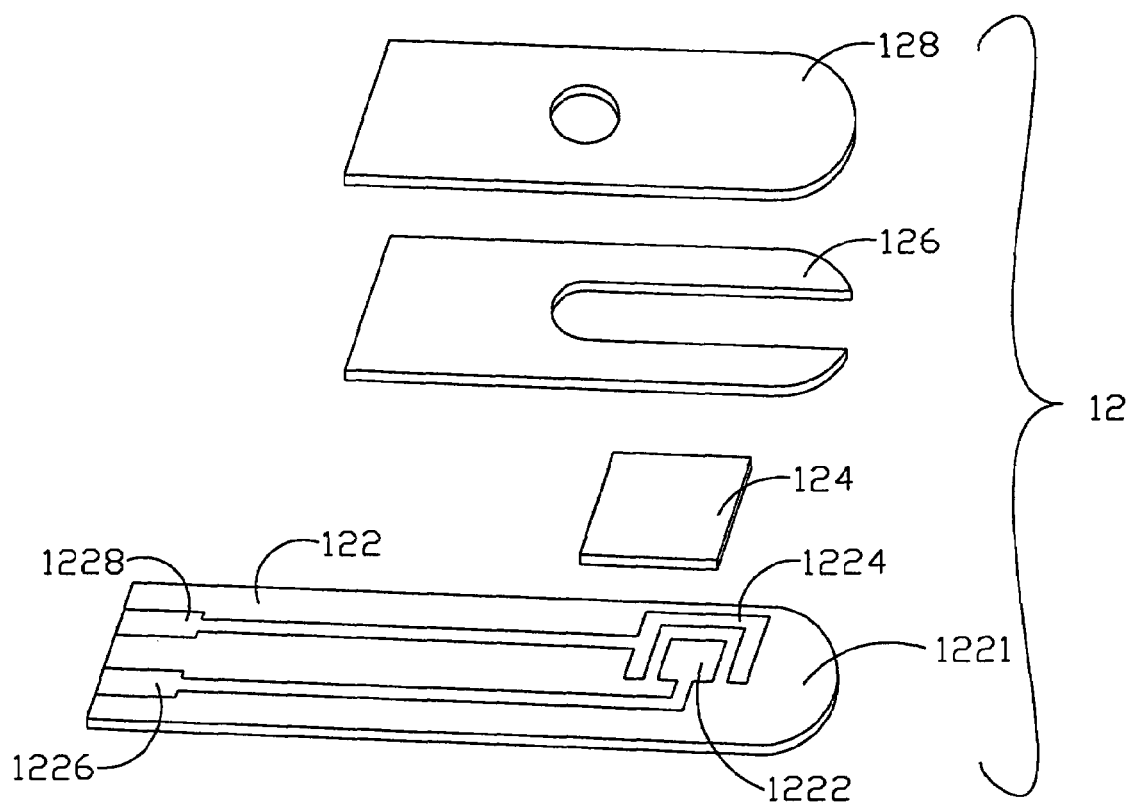
FIG. 2 is an exploded view of a chip of the conventional blood sugar determining instrument of FIG. 1.

The elements of a biosensor of the present invention are substantially the same with those of a general biosensor utilizing a specific catalytic action of enzyme, for example as shown in FIG. 2. The main elements of the present biosensor are like those of the biosensor of FIG. 1 to FIG. 3, including a chip 12 having a resistor $R_s$, a power supply 30, a current/voltage converter 32 having an amplification resistance $R_f$, an analog to digital converter 34, a microprocessor 36 and a display 38. The principal of the present biosensor for monitoring a content of a specific component of a specimen is the same with that of the conventional biosensor of FIG. 1 to FIG. 3, which provides the specimen on the chip 12 plugged into the main detecting unit 10 of the biosensor. Utilizing the result of the enzyme catalytic reaction of the specific component to detect the content of the specific component. Therefore, the kinds of the specific component of the specimen to be detected depend on the enzyme of the reaction layer 124 of the chip 12. For example, when the reaction layer 124 contains glucose oxidase, the biosensor can be utilized to determine the glucose concentration of a blood sample. When the reaction layer 124 contains lactate oxidase, the biosensor can be utilized to determine the lactic acid concentration of saliva. When the reaction layer 124 contains cholesterol oxidase, the biosensor can be utilized to determine the cholesterol concentration of a blood sample. As an example of determining the glucose concentration of the blood sample, when the blood sample is supplied unto the chip 12, the glucose of the blood sample reacts with potassium ferricyanide under catalysis of glucose oxidase. Potassium ferrocyanide in an amount proportional to the glucose concentration of the blood sample is produced. Thus, after a period of time that completion of the enzyme catalytic reaction of glucose of the blood sample, the power supply 30, such as a battery, applies a predetermined voltage $V_{ref}$ to the chip 12. Thereby, the chip 12 generates a time-varying response current I in response to the glucose concentration. That is, the predetermined voltage $V_{ref}$ makes potassium ferrocyanide in the amount proportional to the glucose concentration to proceed oxidation to release electrons. Accordingly, the response current I is generated. The response current I decays as time progresses, and the response current I of each sampling time is converted to an output voltage $V_{out}$ by the current/voltage converter 32. Therefore, the biosensor can detect a voltage-time discharge curve in response to the glucose concentration. The output voltage for each sampling time of the voltage-time discharge curve is converted to a set of binary digital signals. The microprocessor 36 calculates the glucose concentration of the blood sample in accordance with the voltage-time discharge curve and the time of discharge ending thereof. A reading of the glucose concentration is displayed on the display such as the liquid crystal display (LCD) 38.

In another aspect of the present invention, the present invention detects a peak voltage (the maximum output voltage $V_{out}$) upon sensing the specific component of the specimen. Selecting a voltage-time discharge curve corresponding to the peak voltage based on a mapping table of peak voltage versus voltage-time discharge curve established in the microprocessor 36. The time of discharge ending of the voltage-time discharge curve is accordingly determined. The microprocessor 36 calculates the content of the specific component in accordance with the voltage-time discharge curve and the time of discharge ending thereof.

The principle of the present biosensor for monitoring the content of the specific component is the same with that of the general biosensor. However, the present invention provides a method for improving a reading resolution of the biosensor by multi-sampling. The present method selects several neighboring voltages of the voltage-time discharge curve to obtain an average voltage, serving as an output voltage of a selected sampling time among the sampling times corresponding to these neighboring voltages. Thereby, the resolution of the output voltage of each of the sampling times of the voltage-time discharge curve is improved.

The present method will be described in detail in accordance with preferred embodiments with reference to accompanying drawings.

Figure 3:
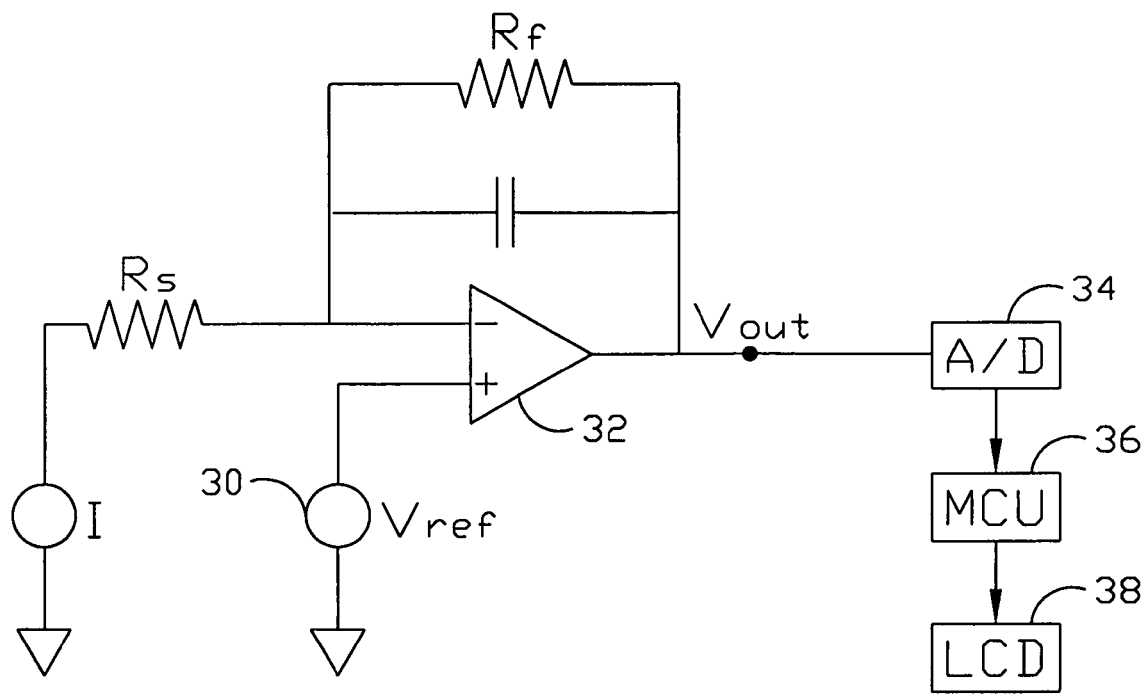
FIG. 3 is a schematic diagram of a control circuit of the conventional blood sugar determining instrument of FIG. 1.
Figure 4:
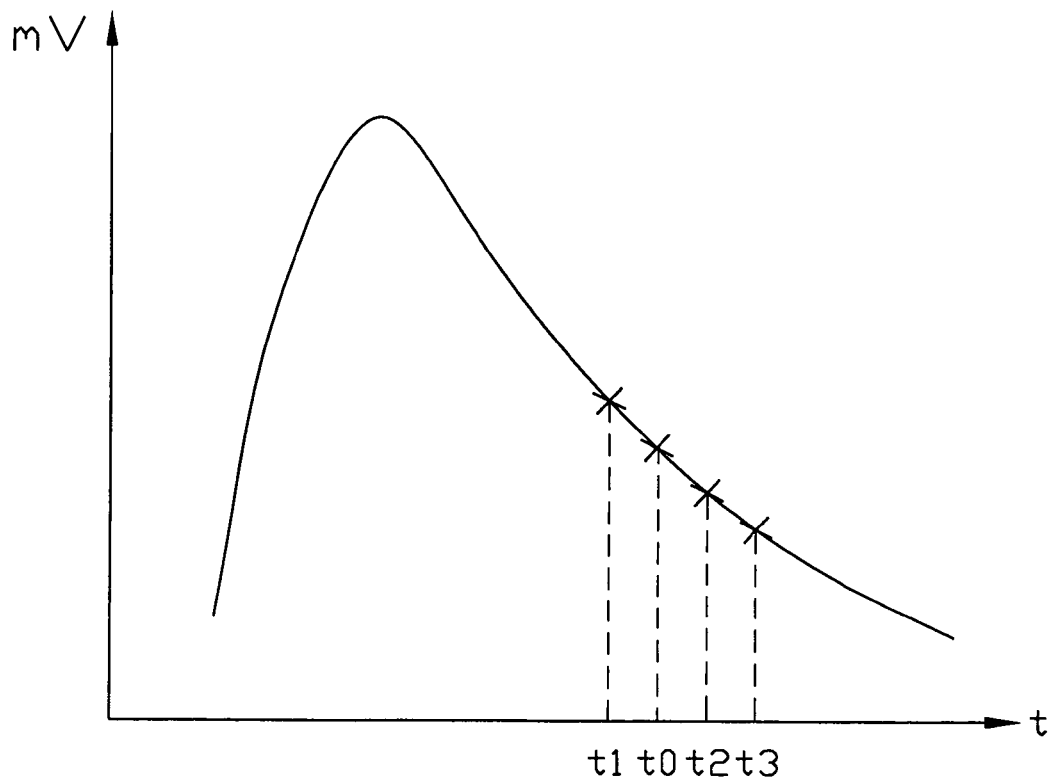
FIG. 4 is a schematic diagram of a voltage-time discharge curve of a specific component of a specimen of the present invention.
Figure 5:
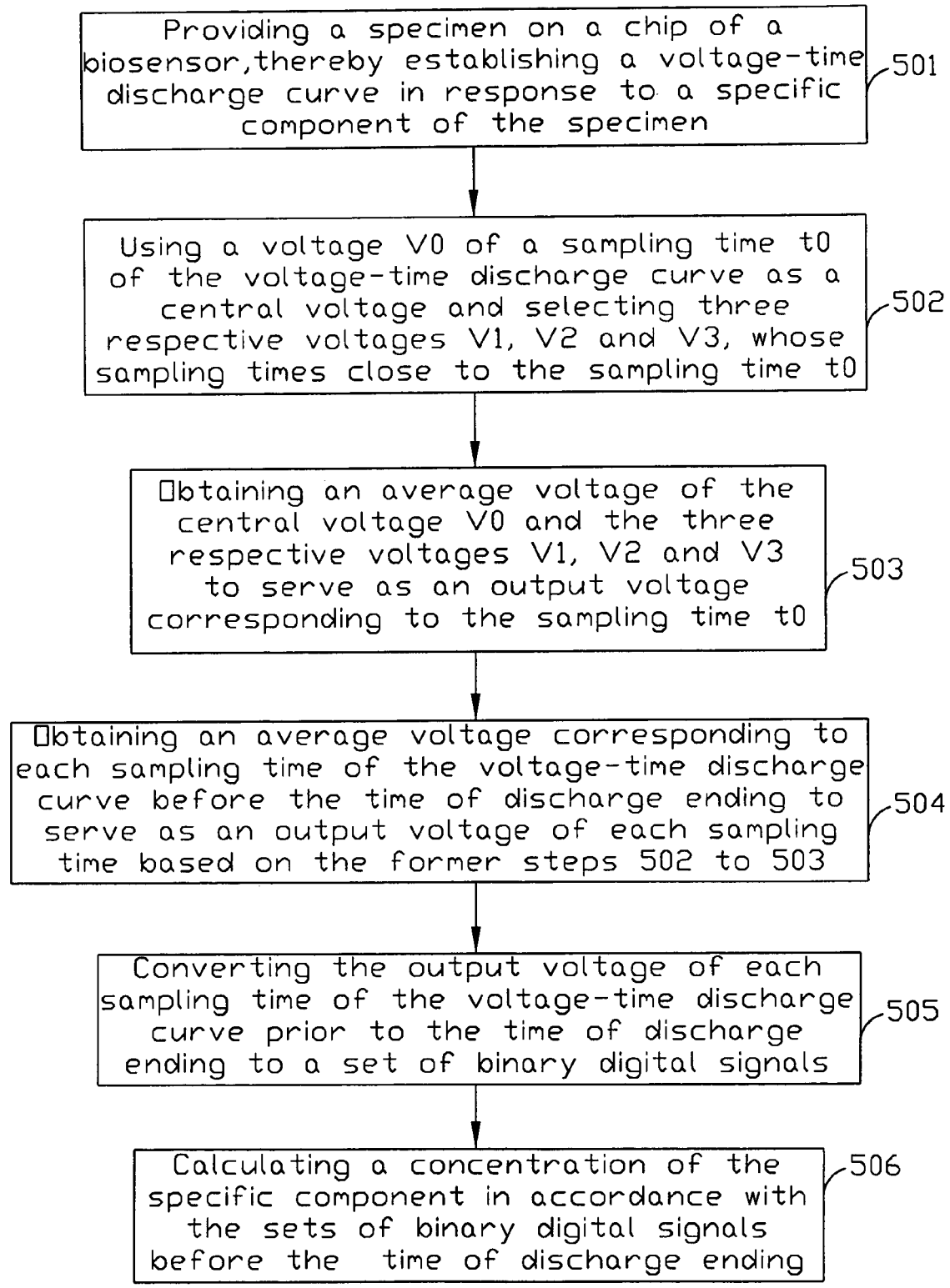
FIG. 5 is a flow chart of the present method according to a first preferred embodiment of the present invention.

Referring to FIG. 4, which shows a voltage-time discharge curve established in response to the specific component of the specimen. FIG. 5 is a flow chart of the present method according to a first preferred embodiment. The first preferred embodiment is described as follows with reference to FIG. 1 to FIG. 3. Firstly, at step 501, providing a specimen on the chip 12 of a biosensor. The chip 12 generates a time-varying response current in response to a specific component of the specimen, so that a voltage-time discharge curve, as shown in FIG. 4, is established in response to the specific component of the specimen. Following, at step 502, using a voltage $V_0$ of a sampling time $t_0$ of the voltage-time discharge curve as a central voltage. Selecting three respective voltages $V_1$, $V_2$ and $V_3$, whose sampling times close to the sampling time $t_0$. At step 503, obtaining an average voltage of the central voltage $V_0$ and the three respective voltages $V_1$, $V_2$ and $V_3$ to serve as an output voltage corresponding to the sampling time $t_0$. For example, using the voltage 101 mv of the sampling time $t_0$ of the voltage-time discharge curve as the central voltage $V_0$, and selecting three respective voltages 103 mv, 100 mv and 99 mv, corresponding to three different sampling times $t_1$, $t_2$ and $t_3$ close to the sampling time $t_0$, of the voltage-time discharge curve. Then, obtaining an average voltage 100.75 mv of the four voltages 103 mv, 101 mv, 100 mv and 99 mv to serve as an output voltage $V_{out}$ of the sampling time $t_0$. The output voltage 100.75 mv of the sampling time $t_0$ is converted to a set of binary digital signals by the analog to digital converter 34. The 100 mv are represented by the former eight bits ($2^0$, $2^1$, $2^2$, $2^3$, $2^4$, $2^5$, $2^6$, $2^7$), and the 0.75 mv is represented by the latter two bits ($2^{-1}$, $2^{-2}$). As a result, the 10-bit digital signals of the output voltage 100.75 mv of the sampling time $t_0$ are (0110010011). The original output voltage of the sampling time $t_0$ prior to multi-sampling average of step 502 to 503 is an integer. However, after processing from step 502 to step 503, the output voltage of the sampling time $t_0$ has accuracy to second decimal point. Moreover, the resolution of bit number of the output voltage of the sampling time $t_0$ increases from 8 bits to 10 bits. The sampling interval at step 502 can be in the range of millisecond or microsecond. The sampling way can be selecting two voltages prior to the central voltage $V_0$ of the sampling time $t_0$ and one voltage behind the central voltage $V_0$, or one voltage prior to the central voltage $V_0$ and two voltages behind the central voltage $V_0$. Alternately, selecting three voltages prior to the central voltage $V_0$, or three voltages behind the central voltage $V_0$.

Following, at step 504, obtaining an average voltage corresponding to each sampling time of the voltage-time discharge curve before the time of discharge ending to serve as an output voltage of each sampling time based on the former steps 502 to 503. Then, at step 505, converting the output voltage of each sampling time of the voltage-time discharge curve prior to the time of discharge ending to a set of binary digital signals by the analog to digital converter 34. Afterward, at step 506, the microprocessor 36 calculates a concentration of the specific component in accordance witch the sets of binary digital signals before the time of discharge ending. A reading of the concentration of the specific component is displayed on the display, for example the liquid crystal display 38. The resolution of the output voltage of each sampling time of the voltage-time discharge curve is improved to second decimal point in accordance with step 502 to step 504. The reading resolution of the concentration of the specific component is thus improved. By the way, the noise interference of the output voltage of each sampling time of the voltage-time discharge curve is also reduced by step 502 to step 504.

Figure 6:
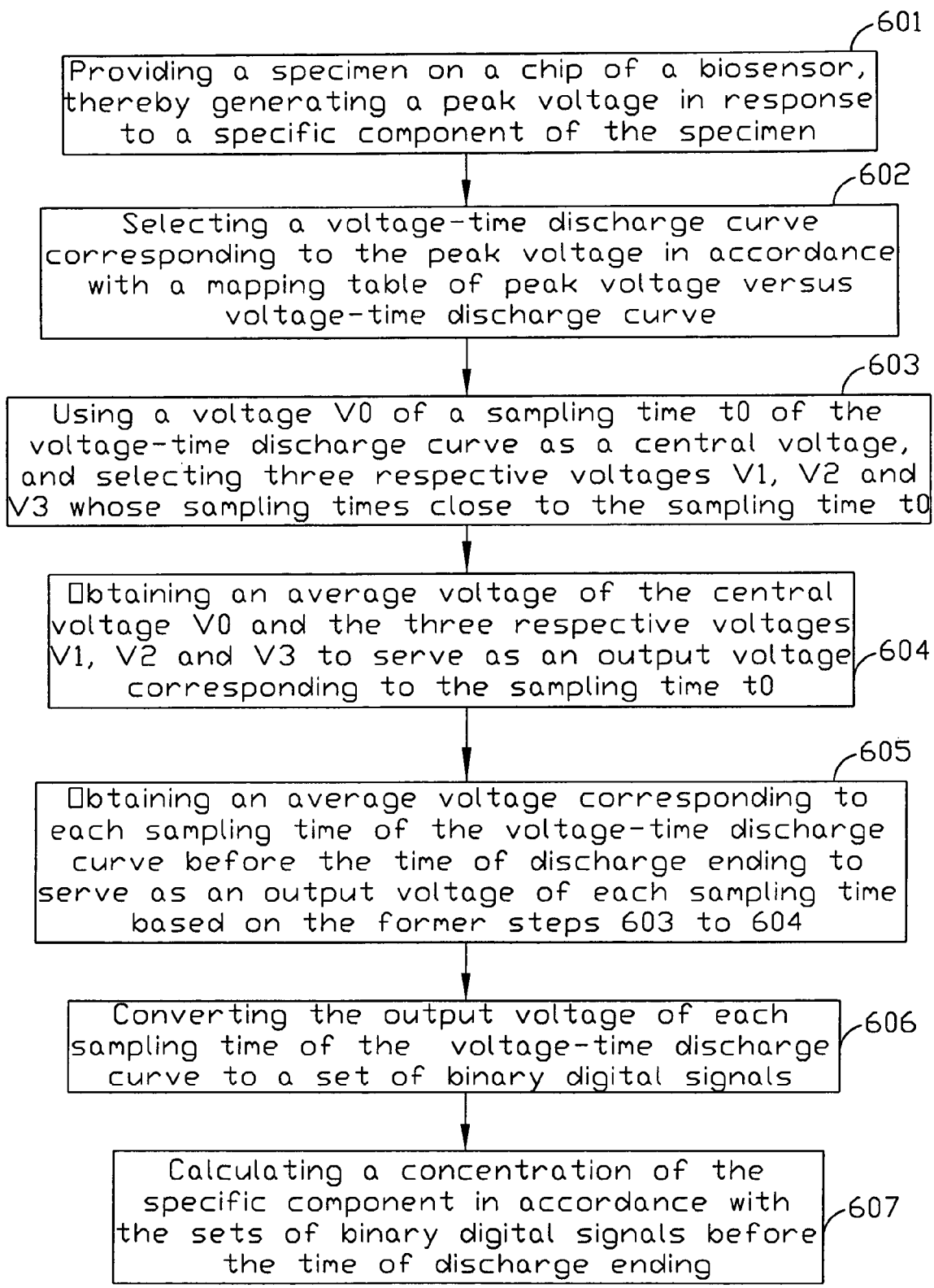
FIG. 6 is a flow chart of the present method according to a second preferred embodiment of the present invention.

FIG. 6 is a flow chart of the present method according to a second preferred embodiment of the present invention, which is described as follows also with reference to the biosensor of FIG. 1 to FIG. 3. At step 601, providing a specimen on the chip 12 of a biosensor, and the chip 12 generates a response current I decaying as time progresses in response to a specific component of the specimen. The response current I gradually decaying is converted to a peak voltage by the current/voltage converter 32. Following, at step 602, selecting a voltage-time discharge curve corresponding to the peak voltage in accordance with a mapping table of peak voltage versus voltage-time discharge curve established in the microprocessor 36. The time of discharge ending of the voltage-time discharge curve is accordingly determined. Then, at step 603, using a voltage $V_0$ of a sampling time $t_0$ of the voltage-time discharge curve as a central voltage. Selecting three respective voltages $V_1$, $V_2$ and $V_3$, whose sampling times close to the sampling time $t_0$. At step 604, obtaining an average voltage of the central voltage $V_0$ and the three respective voltages $V_1$, $V_2$ and $V_3$ to serve as an output voltage corresponding to the sampling time $t_0$. The step 603 of the second preferred embodiment of the present invention corresponds to the step 502 of the first preferred embodiment of the present invention. The sampling interval at step 603 can be in the range of millisecond or microsecond. The sampling way can be selecting two voltages prior to the central voltage $V_0$ of the sampling time $t_0$ and one voltage behind the central voltage $V_0$, or one voltage prior to the central voltage $V_0$ and two voltages behind the central voltage $V_0$. Alternately, selecting three voltages prior to the central voltage $V_0$, or three voltages behind the central voltage $V_0$. Following, at step 605, obtaining an average voltage corresponding to each sampling time of the voltage-time discharge curve before the time of discharge ending to serve as an output voltage of each sampling time based on the former steps 603 to 604. Then, at step 606, converting the output voltage of each sampling time of the voltage-time discharge curve to a set of binary digital signals. At step 607, the microprocessor 36 calculates a concentration of the specific component in accordance with the sets of binary digital signals before the time of discharge ending. A reading of the concentration of the specific component is displayed on the display, for example the liquid crystal display 38.

The present method can be realized by software. It is not necessary to add additional elements in the biosensor. Hence, the purpose of cost down can be attained.

The embodiments are only used to illustrate the present invention, not intended to limit the scope thereof. Many modifications of the embodiments can be made without departing from the spirit of the present invention.

What is claimed is:

1. A method for improving a reading resolution of a biosensor, comprising:

providing a specimen on a chip of a biosensor, wherein the chip generates a peak voltage in response to a specific component of the specimen;

selecting a voltage-time discharge curve corresponding to the peak voltage in accordance with a mapping table of peak voltage versus voltage-time discharge curve;

using a voltage $V_0$ of a sampling time $t_0$ of the voltage-time discharge curve as a central voltage, and selecting a plurality of respective voltages whose sampling times are close to the sampling time $t_0$, thereby obtaining an average voltage of the central voltage $V_0$ and the plurality of respective voltages to serve as an output voltage corresponding to the sampling time $t_0$;

obtaining an average voltage corresponding to each sampling time of the voltage-time discharge curve before the time of discharge ending to serve as an output voltage of each sampling time based on the former step;

converting the output voltage for each sampling time of the voltage-time discharge curve into a set of binary digital signals; and determining a reading of a concentration of the specific component in accordance with the sets of binary digital signals before the time of discharge ending.

2. The method of claim 1, wherein the voltage for each sampling time of the voltage-time discharge curve is an integer.

3. The method of claim 1, wherein the plurality of respective voltages comprises three voltages $V_1$, $V_2$, and $V_3$ close to the central voltage $V_0$ in the voltage-time discharge curve.

4. The method of claim 3, wherein the three voltages $V_1$, $V_2$, and $V_3$ comprise two voltages prior to the central voltage $V_0$ and one voltage behind the central voltage $V_0$ in the voltage-time discharge curve.

5. The method of claim 3, wherein the three voltages $V_1$, $V_2$, and $V_3$ comprise one voltage prior to the central voltage $V_0$ and two voltages behind the central voltage $V_0$ in the voltage-time discharge curve.

6. The method of claim 3, wherein the three voltages $V_1$, $V_2$, and $V_3$ are prior to the central voltage $V_0$ in the voltage-time discharge curve.

7. The method of claim 3, wherein the three voltages $V_1$, $V_2$, and $V_3$ are behind the central voltage $V_0$ in the voltage-time discharge curve.

8. The method of claim 1, wherein the specific component to be determined depends on an enzyme of the chip.

9. The method of claim 1, wherein the sampling interval is in the range of milliseconds.

10. The method of claim 1, wherein the sampling time is in the range of microseconds.

11. An apparatus for improving a reading resolution of a biosensor, comprising:
    means for providing a specimen on a chip of a biosensor, wherein the chip generates a peak voltage in response to a specific component of the specimen;
    means for selecting a voltage-time discharge curve corresponding to the peak voltage in accordance with a mapping table of peak voltage versus voltage-time discharge curve;
    means for using a voltage $V_0$ of a sampling time $t_0$ of the voltage-time discharge curve as a central voltage, and selecting a plurality of respective voltages whose sampling times are close to the sampling time $t_0$, thereby obtaining an average voltage of the central voltage $V_0$ and the plurality of respective voltages to serve as an output voltage corresponding to the sampling time $t_0$;
    means for obtaining an average voltage corresponding to each sampling time of the voltage-time discharge curve before the time of discharge ending to serve as an output voltage of each sampling time based on the former step;
    means for converting the output voltage for each sampling time of the voltage-time discharge curve into a set of binary digital signals; and
    means for determining a reading of a concentration of the specific component in accordance with the sets of binary digital signals before the time of discharge ending.

12. The apparatus of claim 11, wherein the voltage for each sampling time of the voltage-time discharge curve is an integer.

13. The apparatus of claim 11, wherein the plurality of respective voltages comprises three voltages $V_1$, $V_2$, and $V_3$ close to the central voltage $V_0$ in the voltage-time discharge curve.

14. The apparatus of claim 13, wherein the three voltages $V_1$, $V_2$, and $V_3$ comprise two voltages prior to the central voltage $V_0$ and one voltage behind the central voltage $V_0$ in the voltage-time discharge curve.

15. The apparatus of claim 13, wherein the three voltages $V_1$, $V_2$, and $V_3$ comprise one voltage prior to the central voltage $V_0$ and two voltages behind the central voltage $V_0$ in the voltage-time discharge curve.

16. The apparatus of claim 13, wherein the three voltages $V_1$, $V_2$, and $V_3$ are prior to the central voltage $V_0$ in the voltage-time discharge curve.

17. The apparatus of claim 13, wherein the three voltages $V_1$, $V_2$, and $V_3$ are behind the central voltage $V_0$ in the voltage-time discharge curve.

18. The apparatus of claim 11, wherein the specific component to be determined depends on an enzyme of the chip.

19. The apparatus of claim 11, wherein the sampling interval is in the range of milliseconds.

20. The apparatus of claim 11, wherein the sampling time is in the range of microseconds.

* * * * *